United States Patent
Rasmussen et al.

[11] Patent Number: 6,033,377
[45] Date of Patent: Mar. 7, 2000

[54] DEVICE FOR THE ADMINISTRATION OF A LIQUID MEDICAMENT SUSPENSION

[75] Inventors: Thomas Buch Rasmussen, Gentofte; Patric Jannasch, Roskilde; Erling Bonne Jørgensen, Veksø, all of Denmark

[73] Assignee: Novo Nordisk A/S, Bagsvaerd, Denmark

[21] Appl. No.: 09/017,963

[22] Filed: Feb. 3, 1998

[30] Foreign Application Priority Data

Feb. 4, 1997 [DK] Denmark .................................. 0128/97

[51] Int. Cl.$^7$ .................................................. A61M 37/00
[52] U.S. Cl. .............................. 604/82; 604/92; 604/903; 366/130; 366/274
[58] Field of Search .................................. 206/219–221; 604/82, 89, 90, 91, 218, 903; 366/241, 242, 245, 273, 274

[56] References Cited

U.S. PATENT DOCUMENTS 4,850,966  7/1989  Grau et al. .
5,352,036  10/1994  Haber et al. .

Primary Examiner—Wynn Wood Coggins
Assistant Examiner—Deborah Blyveis
Attorney, Agent, or Firm—Steve T. Zelson, Esq.

[57] ABSTRACT

In an ampoule for a medicament the space accommodating the medicament is defined by an ampoule wall (1) a pierceable seal (5) closing one end of the ampoule and a piston (7) closing the other end of the ampoule. A metal containing fixation element (8) is secured to one of the parts defining the medicament accommodating space. A mixing element (9, 10) also containing a metal and having a density larger than 1,0 g/cm$^3$ is movable in medicament accommodating space. At least one of the elements, the fixation element (8) and the mixing element (9, 10), can be attracted by a magnet, and at least one of these elements is a magnetic element, the magnetic strength being so that the mixing element (9, 10) can during normal handling of the ampoule be fixed relative to this ampoule by the magnetic attraction between the fixation element (8) and the mixing element (9, 10) but may be released from its fixed position by manual operation.

15 Claims, 2 Drawing Sheets

DEVICE FOR THE ADMINISTRATION OF A LIQUID MEDICAMENT SUSPENSION

CROSS-REFERENCE TO RELATED APPLICATIONS

This application claims priority under 35 U.S.C. 119 of Danish application 0128/97 filed Feb. 4, 1997, the contents of which are fully incorporated herein by reference.

The present invention relates to a device for the administration of a liquid medicament suspension, and particularly for the administration- of protein, peptide and/or DNA/RNA containing medicament suspension.

Some medications, such as insulin and growth hormones, are administered in the form of suspensions. Insulin for example, is administrated in the form of crystalline suspensions, amorphous non-crystalline suspensions and combination suspensions comprising both crystalline and amorphous forms.

Medicament suspensions, such as the above-mentioned ones, are normally distributed in small containers, such as ampoules or cartridges for pen-systems. Such containers normally comprise more than one dose of ready to use medication. Insulin suspensions are normally distributed in containers containing between 1 and 10 ml. A normal daily dose of insulin is about 6 µl per kg body weight of the user.

Prior to injection, the container is shaken to agitate the liquid suspension, thereby putting any crystals or amorphous particles which may have settled back into suspension. In order to obtain a quick and effective agitation of the suspension, particularly if the suspension is free of air bubbles, an inert glass bead is provided inside the container along with the suspension. Because the glass bead has a density different from that of the suspension, shaking the container causes the glass bead to move within the cartridge and thereby effectively agitate the contents. Such a device is described in e.g. U.S. Pat. No. 4,850,966.

Some medicaments, such as insulin, are more or less adsorbed to the wall of the container. The degree of absorption is largely dependent on the type of medicament or insulin and the surface characteristic of the wall. If insulin, for instance, is injected in low concentrations, such as in infusion liquid, the doctor or physician normally allows for a 30–50% loss of insulin activity due to adsorption to the surface of the container wall, when determining the daily dose for a patient. The percentage loss of insulin activity due to absorption to the surface of the container wall is substantially equal for identical medicaments in identical containers, and it is therefore simple to allow for this factor. High concentration insulin preparations containing about 100 IU/ml of insulin in water solution/suspension should have a biological potency of not less than 95% and not more than 105% of the potency stated on the label. That means that the uncontrolled loss in insulin activity must absolutely not exceed 5%.

Now it has been observed that containers containing glass beads and insulin solutions, as described above, results in a loss of insulin activity which can not be ascribed to the ability of the insulin to be adsorbed to the wall of the container wall, and further it has been observed that the percentage loss of insulin activity due to adsorption to the surface of the container wall differs even for identical medicaments in identical containers. It can therefore be concluded that the glass beads in the container have impact on the loss of insulin activity and result in uncontrolled loss of insulin activity.

The object of the present invention is to provide a device for the administration of a liquid medicament suspension which is suitable for storage, in which the medicament can be homogenized easily, and which does not result in uncontrolled loss of medicament activity.

This object is achieved by a device for the administration of a medicament suspension, comprising a container containing a liquid medicament suspension and having a container wall with an inner and an outer surface, a fixations element, and at least one mixing element disposed in the container; said at least one mixing element comprising a metal, at least one of said metal containing fixations element and said metal containing mixing element being capable of being attracted by a magnet and the other of said metal containing fixations element and said mixing element being a magnetic element;

the mixing element being dimensioned relative to the size of the container such that the suspension is homogenized by shaking movements of the container, preferably said at least one mixing element having a volume relative to the container volume of at least 0.01% and a density which is greater than the density of the suspension, preferably a density of at least 1,0 g/cm$^3$;

the magnetic element having a magnetic strength so as to be able to secure the mixing element in a fixed position relative to the container during normal handling of the device, said device being manually operable to release the mixing element from the fixed position.

The invention also relates to a device for the administration of a medicament suspension, comprising a container for receiving a liquid medicament suspension and having a container wall with an inner and an outer surface, a fixations element, and at least one mixing element disposed in the container;

said mixing element having a volume relative to the container volume of at least 0.01%, a density of at least 1.0 g/cm$^3$ and comprising a metal, at least one of said metal containing fixations element and said metal containing mixing element being capable of being attracted by a magnet and the other of said metal containing fixations element and said mixing element being a magnetic element;

the magnetic element having a magnetic strength so as to be able to secure the mixing element in a fixed position relative to the container during normal handling of the device, said device being manually operable to release the mixing element from the fixed position.

The magnetic element referred to throughout the application is most preferably a permanent magnet, containing one or more ferromagnetic materials and/or one or more ferrimagnetic materials. Magnetic elements containing one or more ferrimagnetic materials are preferably ceramic magnets containing metal oxides, such as ferrites.

It has surprisingly been found that the above-defined device of the invention for the administration of a liquid medicament suspension is suitable for storage, and further that the medicament can be homogenized easily without uncontrolled loss of medicament activity.

As a result of the observation, that device of the invention does not give rise to uncontrolled loss of medicament activity, it was concluded that the uncontrolled loss of medicament activity in the prior art devices, such as the device of U.S. Pat. No. 4,850,966, was caused by the free movement of the glass bead in the container.

The inventors of the present invention have observed that the movement of a bead in the medicament suspension results in a decomposition of the active medicament, probably due to a transfer of energy from the bead to the active medicament. Later studies have confirmed this theory, and it has been visually observed that the medicament is denatured if the suspension is in contact with a moving bead for a substantial period.

The invention is therefore particularly useful when the device is a syringe and particularly a pen-system, because such syringes and particularly pen-systems are often carried by the doctor or the user for hours or days prior to the use of them.

At least one of the metal containing fixations element and the metal containing mixing element is a magnetic element. The requirement to the other of the fixations element and the mixing element is that it should be able to be attracted to a magnet. If both of the fixations element and the mixing element are magnetic elements, they should be attracted to each other.

The device of the invention may comprise several mixing elements. Preferably, the device comprises one, two or three mixing elements, the mixing elements preferably having the same size. Most preferably, the device comprises one mixing element.

The device is described below as having only one mixing element, however, it should be understood that the described embodiments also could have more than one mixing element.

The mixing element preferably has a volume relative to the container volume of at least 0.05%, most preferably of at least 0.1% and preferably a density of at least 1,5 g/cm$^3$.

The mixing element may have any suitable shape. Preferably, the mixing element is free of any sharp corners and edges, and most preferably the mixing element has a spherical shape, and even more preferably a spherical shape with a diameter between 1 and 4 mm.

The mixing element may be made from any suitable material or combination of materials, provided that the material is magnetic and/or is capable of being attracted by a magnet, or the combination of materials comprise at least one material which is magnetic and/or capable of being attracted by a magnet and that the surface of the mixing element is of material which is inert to the medicament suspension.

In this context the term "inert" denotes a material which, by simple contact with the medicament preparation, interacts neither chemically nor physically in a manner substantially interfering with the medicament preparation.

Preferably, the mixing element is made from a metal selected from barium ferrite, strontium ferrite, silicon ferrite, AlNiCo alloys, SmCo alloys, carbon steel, $BaFe_{12}O_{18}$, iron, permalloy (Ni—Fe), superpermalloy (Ni—Fe—Mo), ferroxcube A(Mn, Zn)$Fe_2O_4$, ferrocube B(Ni, Zn)$Fe_2O_4$ and $Fe_3O_4$, optionally coated with a polymer material, preferably selected from mono- or copolymerized polyolefins including cyclic and bicyclic polyolefins.

The container preferably has a cylindrical shape with a distal and a proximal end portion, said distal end portion comprising a pierceable seal. Preferably, the container is a syringe house, an ampoule or cartridge, wherein, the proximal end is closed by a movable piston.

According to the invention the mixing element is immobilized in the container during normal handling, and the device can be operated manually so as to release the mixing element from the fixed position.

In one embodiment the magnetic element has a strength relative to the mixing element such that it is possible to manually shake the mixing element free of its fixed position. Preferably, the magnetic force between the fixations element and the mixing is between 0.6 mN and 500 N, more preferably between 1 and 500 mN, and most preferably between 2 and 50 mN. When the shaking and optionally the injection are completed, the device is held in a position which enables the fixations element to reimmobilizise the mixing element. In this embodiment, the fixations element is preferably fixed to the outer or the inner surface of the container. Preferably, the fixations element is fixed to the distal end portion of the container or to the piston, if any.

In an alternative embodiment, the device according to the invention can be operated manually so as to separate the magnetic element and the container from each other, thereby releasing the mixing element from the fixed position.

The magnetic force between the fixations element and the mixing is preferably between 0.6 mN and 500 N, more preferably between 100 mN and 100 N, and most preferably between 1 and 50 N.

In a further embodiment the device is in the form of a syringe including
  a syringe house for receiving a container containing a liquid medicament suspension and at least one mixing element disposed in the container, said mixing element having a density which is greater than the density of the suspension and comprising a metal capable of being attracted by a magnet or being a magnetic element, said at least one mixing element being dimensioned relative to the size of the container such that the suspension is homogenized by shaking movements of the container and
  a needle assembly coupled to a distal end of the housing, and
  a removable protective cap;
  said cap comprising a fixations element being able to be attracted to a magnetic element or preferably being a magnetic element having a magnetic strength of at least 1 mT.

The syringe according to the invention preferably comprises a plunger rod and means for measuring the distance which the plunger rod travels to determine the amount of liquid dispensed and means for adjustment of the dose to be injected.

In a variation of the above syringe of the invention, the device is a syringe including a syringe house containing the container and a needle assembly coupled to a distal end of the housing and including a removable protective cap, said fixations element being fixed to the cap, and the device can, by detaching the cap, be operated manually so as to separate the fixations element and the container from each other, thereby releasing the mixing element from the fixed position. In this embodiment it is preferred that the fixations element is a magnetic element. This embodiment may also preferably comprise a plunger rod and means for measuring the distance which the plunger rod travels to determine the amount of liquid dispensed and means for adjustment of the dose to be injected.

The invention also relates to a container for use in combination with a syringe as described above.

The device or syringe of the invention is most preferably a pen for the administration of insulin crystal suspension.

The invention will be described in greater detail below with reference to the accompanying drawings.

DETAILED DESCRIPTION OF THE INVENTION

Figure 1:
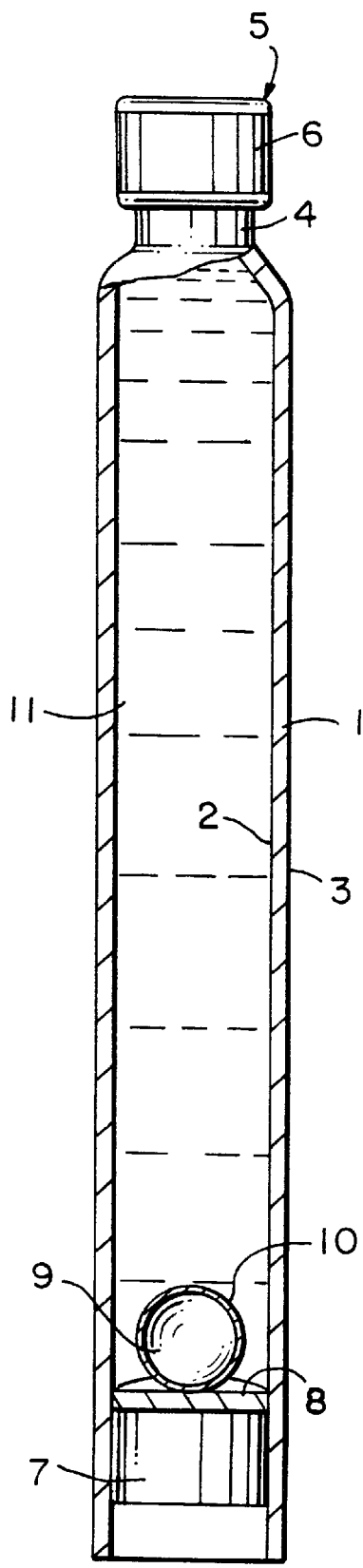
FIG. 1 is a partly cross-sectional view of a first embodiment of the device according to the invention in the form of a cylindrical ampoule containing a medicament suspension.

The ampoule shown in FIG. 1 comprises a wall 1 defining the hollow, cylindrical shape of the ampoule-body. The wall may be of any suitable material such as glass or polymer. The wall 1 has an inner surface 2 and an outer surface 3. At the distal end portion of the ampoule, it has a neck 4 and a seal 5. The seal 5 comprises a pierceable seal (not shown), such as a rubber seal covering the distal end of the ampoule. The pierceable seal is fixed to the container by use of a sealing strip 6 covering at least a part of the neck 4.

The proximal end is closed by a movable piston 7 comprising a fixations element in the form of a plate 8 at its distal end. The fixations element 8 is preferably a magnetic element made from barium ferrite, strontium ferrite, silicon ferrite, AlNiCo alloys, SmCo alloys, carbon steel, $BaFe_{12}O_{18}$, iron, permalloy (Ni—Fe), superpermalloy (Ni—Fe—Mo), ferroxcube A(Mn, Zn)$Fe_2O_4$, ferrocube B(Ni, Zn)$Fe_2O_4$ or $Fe_3O_4$, and is fixed to the piston 7 by use of an adhesive material. In an alternative embodiment the fixations element is fixed to the piston by a snap lock. The fixations element in the form of a magnetic plate may preferably have a strength of at least 1 mT.

The ampoule contains a bead 9 of a material which is attracted to the fixations element 8 in the form of a magnetic plate or the mixing element being a magnetic element having a strength of at least 1 mT. The magnetic force between the fixations element and the mixing is between 0.6 mN and 500 N, and the mixing element is thereby secured in a fixed position when the ampoule is not shaken. The bead is preferably made from barium ferrite, strontium ferrite, silicon ferrite, AlNiCo alloys, SmCo alloys, carbon steel, $BaFe_{12}O_{18}$, iron, permalloy (Ni—Fe), superpermalloy (Ni—Fe—Mo), ferroxcube A(Mn, Zn)$Fe_2O_4$, ferrocube B(Ni, Zn)$Fe_2O_4$ or $Fe_3O_4$ and comprises a surface coating 10 of a polyolefin material, the average density of the bead being greater than the density of the medicament suspension.

The bead 9 has a spherical shape, and in the figures the bead has a diameter of about ⅔ relative to the diameter of the ampoule-body. However, it is preferred that the bead is as small as possible, preferably having a diameter from 1/10 to ⅔ relative to the diameter of the ampoule-body.

The ampoule also comprises a liquid medicament suspension 11, preferably an aqueous suspension, having a density of approximately 1 g/cm³ or a little more, e.g. 1.05 g/cm³. It is most preferred that the medicament suspension is an aqueous insulin crystal suspension.

As shown in FIG. 1, the bead 9 is secured in a fixed position relative to the ampoule by magnetic force. However, when shaking the ampoule manually, the magnetic element, which may be the bead 9 or the plate 8 is not strong enough to secure the bead 9 in the fixed position and the bead 9 escapes from the magnetic fixation and thereby acts as a mixing element, homogenizing the suspension. It should be observed that in another embodiment, both the bead 9 and the plate 8 may be magnetic elements.

When the suspension is homogenized, it is ready for injection. The medicament may be sucked into a syringe and injected from there, or the ampoule may be used as a cartridge in a pen-system. Prior to, during or after the injection the ampoule is held in an upright position so as to make the bead 9 fall back onto the fixations element 8 to which it is secured by magnetic force.

Figure 2:
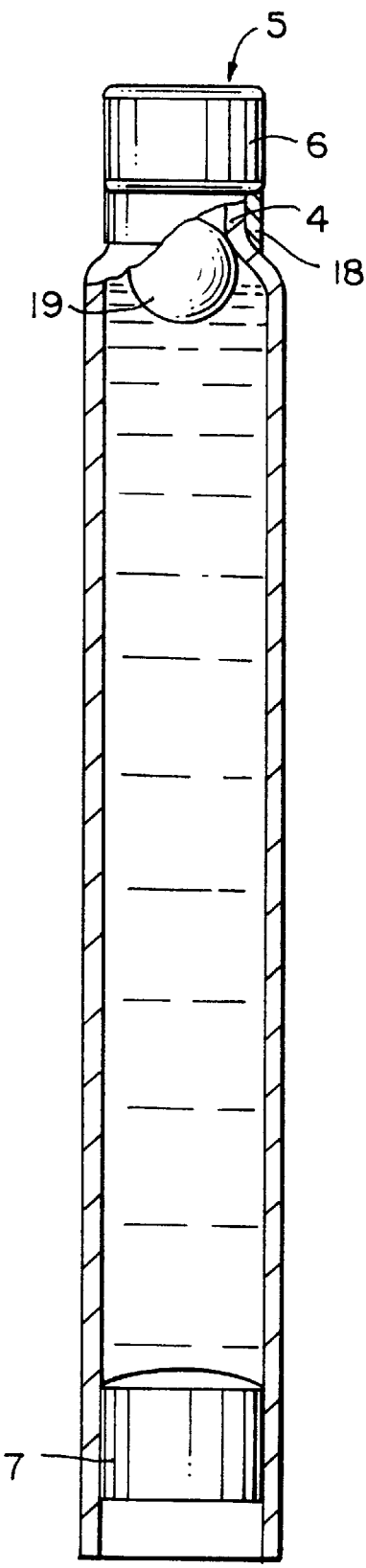
FIG. 2 is a partly cross-sectional view of a second embodiment of the device according to the invention in the form of a cylindrical ampoule containing a medicament suspension.

FIG. 2 shows an alternative embodiment of the invention. The ampoule shown in FIG. 2 differs from the ampoule of FIG. 1 only in the location of the fixations element, and further the bead does not comprise an outer coating.

The ampoule of FIG. 2 comprises a wall 1 defining the hollow, cylindrical shape of the ampoule-body and having an inner surface 2 and an outer surface 3. At the distal end portion of the ampoule, it has a neck 4 and a sealing 5 with a not shown pierceable seal which is fixed to the container by use of a sealing strip 6.

Around the neck 4, the ampoule comprises a fixations element in the form of a magnetic ring 18 preferably made from barium ferrite, strontium ferrite, silicon ferrite, AlNiCo alloys, SmCo alloys, carbon steel, $BaFe_{12}O_{18}$, iron, permalloy (Ni—Fe), superpermalloy (Ni—Fe—Mo), ferroxcube A(Mn, Zn)$Fe_2O_4$, ferrocube B(Ni, Zn)$Fe_2O_4$ or $Fe_3O_4$. The ring is preferably fixed to the neck 4 by use of the sealing strip 6. In an alternative embodiment, the magnetic ring is fixed to the piston by a snap lock. The magnetic ring may preferably have a strength of at least 1 mT.

The proximal end is closed by a movable piston 7, and the ampoule also comprises a medicament suspension 11.

The ampoule contains a bead 19 with a spherical shape. The bead 19 is of a material which is attracted to the magnetic ring 18 and thereby secured in a fixed position at the distal end portion of the ampoule.

In an alternative embodiment of the one shown in FIG. 2 the bead 19 is a magnetic element, having a strength of at least 1 mT and the ring 18 may be non-magnetic.

Figure 3:
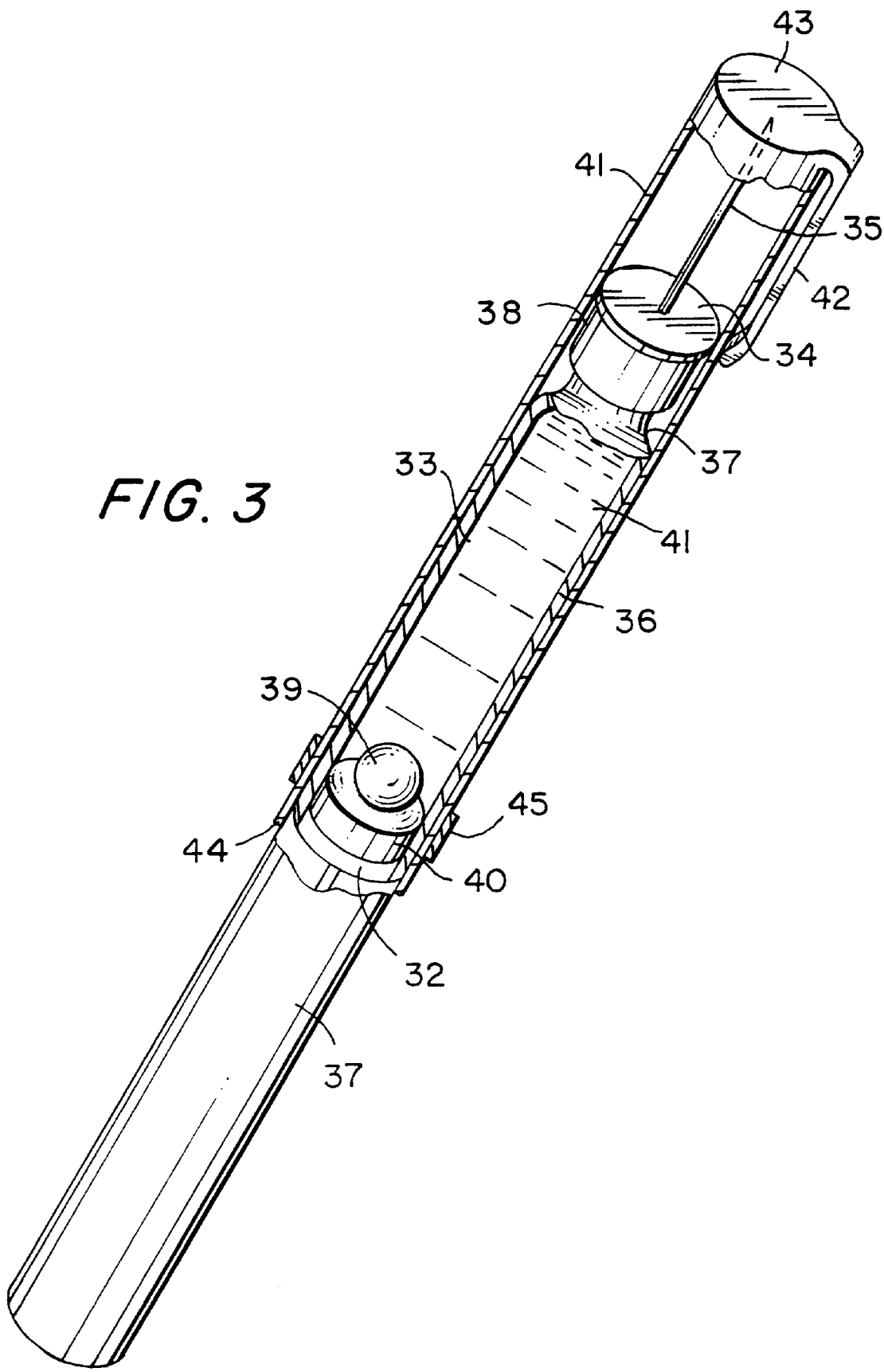
FIG. 3 is a perspective, partly cross-sectional view of a third embodiment of the device according to the invention in the form of an injection-pen comprising a cartridge with a medicament suspension.

The embodiment of the invention shown in FIG. 3 is a syringe in the form of a pen-system comprising a dose setting means 31 (not shown), which may be of any type, and a plunger rod 32, the movement of the plunger rod 32 being controlled by the dose setting means 31. Such dose setting means are well-known in the art and are e.g. described in U.S. Pat. Nos. 5,226,895, 4,973,318 and EP 327 910.

The pen-system further comprises a replaceable cartridge 33 and a needle assembly 34 having a doubled ended needle 35. The cartridge 33 comprises a wall 36 defining the hollow, cylindrical shape of the cartridge-body, a distal end portion having a neck 37, and a seal 38 with a pierceable seal (not shown) covering the distal end of the cartridge 33.

The ampoule contains a bead 39 with a spherical shape. The bead 19 is of a material which is capable of being attracted by a magnet. The proximal end of the cartridge 33 is closed by a movable piston 40, and the cartridge also comprises a medicament suspension 41.

The needle assembly 34 is secured to the distal end of the cartridge 33 by the proximal end of the needle penetrating the pierceable seal.

The pen-system further comprises a detachable cap 41 for shielding the needle 35. The cap 41 comprises a clip 42 which provides a convenient means for holding the pen-system in a pocket.

The cap 41 has a hollow cylindrical shape with a distal closed end 43 and a proximal open end defined by the encircling distal edge 44 of the cap. A displaceable fixations element in the form of a magnetic ring 45 is secured along the encircling edge 44, at the same level as the distal surface of the piston of the cartridge 33 when the cap is on. The ring 45 is preferably made from barium ferrite, strontium ferrite, silicon ferrite, AlNiCo alloys, SmCo alloys, carbon steel, $BaFe_{12}O_{18}$, iron, permalloy (Ni—Fe), superpermalloy (Ni—Fe—Mo), ferroxcube A(Mn, Zn)$Fe_2O_4$, ferrocube B(Ni, Zn)$Fe_2O_4$ or $Fe_3O_4$, and is fixed to the cap 41 by a tongue (not shown) in the ring 45 engaged in a groove in the cap, extending from about 0.5 cm from its proximal end and to about 3 cm from its distal end so that the ring 45 may be positioned at the same height as the distal surface of the piston 40 irrespective of the filling degree of the cartridge 33. In alternative embodiments the magnetic ring may be fixed to the cap by any other suitable means, such as by a metal strip in the cap.

When the cap 41 is on, the bead 39 is secured in a fixed position relative to the cartridge by magnetic force. Due to the attraction between the ring 45 and the bead 39, the ring will be easy to position so as to be at the same height as the distal surface of the piston 40 and thereby be at the same height as the bead.

When using the pen-system, the cap 41 including the magnetic ring 45 is removed. The bead is now free of the magnetic ring, and the pen-system is shaken and the suspension is homogenized. After injection the pen-system is held in an upright position and the cap is put on. Due to low friction between the cap 41 and the ring 45, the magnetic ring 45 may automatically be positioned at the same height as the bead 39, or if the friction is too high, the ring 45 may be manually positioned. In order to ensure that the ring 45 is correctly positioned, the cap 41 may comprise a transparent window.

TEST EXAMPLE 4 cartridges having a cylindrical shape, with an inner diameter of about 9.25 mm and filled with 3 ml of an insulin suspension, were tested in 4 different set up:

a) The cartridge contained a mixing element 1 (an iron ball, 2 mm in diameter).

b) The cartridge contained a mixing element 2 (a glass ball, 2,5 mm in diameter).

c) The cartridge did not contain any mixing element.

d) The cartridge contained, according to the invention, a mixing element 1 (an iron ball, 2 mm in diameter), fixed in the cartridge by use of a magnetic fixing element, placed on the outer side of the cartridge.

The cartridges were rotated (30 rpm), 4 hours a day, at 37° C. for 11 days. The insulin activity in the suspensions from setups a)–d) were analysed with a USP recommended HPLC method:

a) 75%±5%(n=9)

b) 77%±5%(n=9)

c) 99.8%±1%(n=9)

d) 99.5%±1%(n=9).

We claim:

1. A device for the administration of a medicament suspension comprising:

a container for storing a liquid medicament suspension having a longitudinal axis;

a fixations element axially secured against movement to said container during normal storage and handling of said device; and a mixing element disposed in said container for movement along said axis;

wherein one of said elements comprises a magnetic material and the other of said elements comprises a material magnetically attracted to said one element, and wherein the magnetic attraction between said elements has a strength such that said mixing element remains substantially fixed within said container during normal handling of the device, but which allows said mixing element to move axially relative to said fixations element within said container when said device is shaken in order to mix the contents of the container.

2. A device according to claim 1, wherein the magnetic force between said elements is between 0.6 mN and 500 N.

3. A device according to claim 2, wherein the magnetic force between said elements is between 1 mN and 500 mN.

4. A device according to claim 3, wherein the magnetic force between said elements is between 2 mN and 50 mN.

5. A device according to claim 1, wherein said fixations device is secured within said container.

6. A device according to claim 5, wherein said container includes a piston which is axially moveable for administering a medicament suspension within said container, but which is axially stationary during normal storage and handling of said device, and wherein said fixations device is secured to said piston.

7. A device according to claim 1, wherein said container has a distal end having a neck portion, and wherein said fixations device is secured about said neck portion.

8. A device according to claim 1, wherein said container contains a liquid medicament suspension and said mixing element has an outer surface which is inert to the medicament suspension.

9. A device according to claim 8, wherein said suspension is an insulin suspension.

10. A device according to claim 1, wherein said mixing element is spherical and has a diameter between 1 and 4 mm.

11. A device according to claim 1, wherein said mixing element has a metal core and is coated with a polyolefin material.

12. A device according to claim 1, wherein said other element also comprises a magnetic material.

13. A device according to claim 1, wherein said mixing element has a volume relative to the container volume of at least 0.01% and a density of at least 1.0 g/cc.

14. A method of storing a liquid medicament suspension, comprising the steps of:

(a) providing a container having a longitudinal axis;

(b) disposing a liquid medicament suspension within said container;

(c) providing a mixing element and a fixations element, wherein one of said elements comprises a magnetic material and the other of said elements comprises a material magnetically attracted to said one element, (d) disposing said mixing element in said container so as to be axially moveable therein;

(e) securing said fixations element to said container against axial movement during normal storage and handling of said device; and (f) storing said liquid medicament with said fixations element secured to said container, wherein sufficient magnetic material is provided in said one element that the magnetic attraction between said elements has a strength such that said mixing element remains substantially fixed within said container during normal handling of the device while said medicament remains stored.

15. A method according to claim 13, wherein sufficient magnetic material is provided in said one element that the magnetic attraction between said elements has a strength which allows said mixing element to move relative to said fixations element within said container when said device is shaken, when it is desired to mix the contents of the container, without having to remove said fixations element.

* * * * *